United States Patent [19]

Iyama et al.

[11] Patent Number: 5,698,717
[45] Date of Patent: Dec. 16, 1997

[54] PROCESS FOR PREPARING HYDROXYFLAVAN COMPOUNDS

[75] Inventors: Hironobu Iyama, Osaka; Naoki Inui, Yamatokoriyama; Kyoko Tsuta, Kawanishi; Hideo Nagasaki, Osaka; Manji Sasaki, Nishinomiya, all of Japan

[73] Assignee: Sumitomo Chemical Company, Limited, Osaka, Japan

[21] Appl. No.: 808,673

[22] Filed: Feb. 28, 1997

Related U.S. Application Data

[63] Continuation of Ser. No. 493,388, Jun. 21, 1995, abandoned.

[30] Foreign Application Priority Data

Jun. 23, 1994 [JP] Japan ..................... 6-141760

[51] Int. Cl.⁶ .................... C07D 311/60; C07D 311/64
[52] U.S. Cl. .................................................. 549/406
[58] Field of Search ...................................... 549/406

[56] References Cited

FOREIGN PATENT DOCUMENTS

| 0505987 | 9/1992 | European Pat. Off. . |
| 582309 | 2/1994 | European Pat. Off. . |
| 55-139375 | 10/1980 | Japan . |
| 56-5476 | 1/1981 | Japan . |
| 57-16877 | 1/1982 | Japan . |
| 61-27979 | 2/1986 | Japan . |
| 61-27980 | 2/1986 | Japan . |
| 05032654 | 2/1993 | Japan . |
| 5-32654 | 2/1993 | Japan . |
| 822659 | 10/1959 | United Kingdom . |

*Primary Examiner*—Johann Richter
*Assistant Examiner*—Laura L. Stockton
*Attorney, Agent, or Firm*—Watson Cole Stevens Davis, PLLC

[57] ABSTRACT

Described herein is a process for preparing a hydroxyflavan compound which comprises reacting a polyhydric phenol compound represented by formula(2):

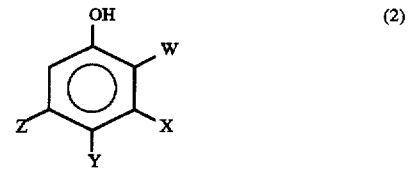

(2)

wherein at least one of W, X, Y and Z is hydroxy; with a ketone in the presence of (i)an acid catalyst and (ii)water and/or a seed crystal, using an organic solvent which is insoluble in water, procuces the hydroxyflavan compounds in high yield and with high selectivity while maintaining high conversion of the polyhydric phenol.

16 Claims, No Drawings

PROCESS FOR PREPARING HYDROXYFLAVAN COMPOUNDS

This application is a Continuation of application Ser. No. 08/493,388, filed Jun. 21, 1995 now abandoned.

BACKGROUND OF THE INVENTION

1. Field of the Invention

The present invention relates to a new process for the preparation of hydroxyflavan compounds. The invention provides a process for preparing hydroxyflavan compounds represented by the formula(1):

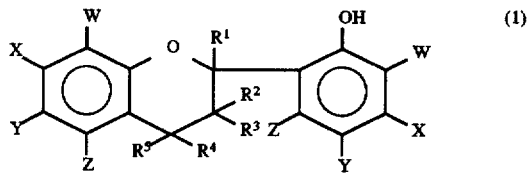

wherein $R^1$, $R^4$ and $R^5$ each independently represent alkyl, cycloalkyl, aralkyl or aryl, and $R^2$ and $R^3$ each independently represent hydrogen, alkyl, cycloalkyl, aralkyl or aryl, or $R^1$ and $R^2$ together with the carbon atoms to which they are attached form a cycloalkane ring, or $R^4$ and $R^5$ together with the carbon atom to which they are attached form a cycloalkane ring; end W, X, Y and Z each independently represent hydrogen, halogen, hydroxy, alkyl, alkenyl, cycloalkyl, aralkyl, arylalkenyl or aryl, provided that at least one of W, X, Y and Z is hydroxy. In more detail, the present invention relates to a process for preparing the hydroxyflavan compounds of formula(1) comprising a condensation reaction of a polyhydric phenol and a ketone, which exhibits high yield and high selectivity(explained below) while keeping high conversion of polyhydric phenol,

2. Related Art

Various processes for preparing hydroxyflavan compounds of formula(1) have been proposed in many documents such as GB 822,659, JP-A-55-1339375, JP-A-56-5476, JP-A-57-16877, JP-A-57-114585, JP-A-61-27979, JP-A-61-27980, JP-A-B-32654 and EP-A-582,309(=JP-A-6-56814). According to the known processes, the hydroxyflavan compounds is usually prepared by a condensation reaction of a polyhydric phenol represented by the formula (2):

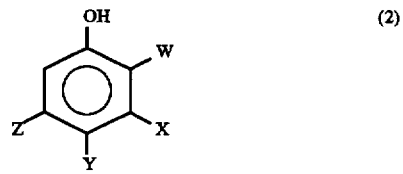

wherein W, X, Y and Z are as defined above, and a ketone. For example, GB 822,659 discloses a process comprising reacting a polyhydric phenol with acetone in the presence of an inorganic acid as catalyst, using water as reaction solvent. JP-A-55-139375 discloses a process comprising reacting resorcin with an aliphatic ketone, the molar ratio of resorcin to ketone being 3 or more, in the presence of an inorganic acid as catalyst. JP-A-56-5476 discloses a process comprising reacting resorcin with an aliphatic ketone in the presence of an acid catalyst such as a cation exchange resin. JP-A-57-16877 and JP-A-57-114585 disclose a process comprising a condensation reaction of resorcin with an α, β-unsaturated aliphatic ketone. JP-A-61-27979 discloses a process comprising reacting resorcin with an aliphatic ketone in the presence of an acid catalyst and a neutral salt. JP-A-61-27980 discloses a process comprising conducting a condensation reaction of resorcin with an aliphatic ketone while controlling the rate of addition of the ketone to the reaction mixture. JP-A-5-32654 discloses a process comprising reacting resorcin with a ketone in the presence of an acid catalyst, using methanol as reaction solvent. EP-A-582, 309(=JP-A-6-56814) discloses a process comprising reacting pyrogallol with a ketone in the presence of an acid catalyst, using an organic solvent such as an acetic acid ester.

In the reaction of polyhydric phenol with ketone as mentioned above, in order to improve the yield of the hydroxyflavan compound of formula(1) based on the amount of polyhydric phenol charged into the reaction mixture, both the conversion of the polyhydric phenol and the selectivity need to be improved. The conversion of the polyhydric phenol is defined as the ratio of the amount of the polyhydric phenol reacted with ketone during the reaction to the total amount of the polyhydric phenol charged in the reaction mixture. The selectivity is defined as the ratio of the amount of polyhydric phenol reacted with ketone to produce the hydroxyflavan compound of formula(1) to the total amount of polyhydric phenol reacted with ketone.

However, known processes as mentioned above have drawbacks. That is, in order to improve selectivity, molar ratio of polyhydric phenol to ketone need to be increased as to about 2.2–3.3, but the increase of molar ratio lowers conversion of the polyhydric phenol and, as the result, yield of the hydroxyflavan compounds of formula(1) based on amount of polyhydric phenol charged into the reaction mixture is also lowered. On the other hand, a decrease of the molar ratio of polyhydric phenol to ketone to about 1 accelerates production of resinous materials and lowers the selectivity. As the result yield of hydroxyflavan compounds of formula(1) is also lowered.

The inventors of the present invention have conducted extensive studies to solve the above-mentioned drawbacks of known processes and, as a result, have accomplished the present invention.

An object of the present invention is to provide a process for preparing hydroxyflavan compounds of formula(1) which exhibits high conversion of polyhydric phenol, high selectivity and, as the result, high yield of the hydroxyflavan compounds.

SUMMARY OF THE INVENTION

The present invention provides a process for preparing a hydroxyflavan compound of formula(1) which process comprises reacting a polyhydric phenol compound of formula(2) with a ketone in the presence of (i)an acid catalyst and (ii)water and/or a seed crystal, using an organic solvent which is insoluble in water.

That is, the characteristics of the present invention reside in conducting the condensation reaction in the presence of an acid catalyst and water or seed crystal, using an organic solvent which is insoluble in water in order to improve conversion of the polyhydric phenol, selectivity and yield of hydroxyflavan compounds of formula(1).

DETAIL DESCRIPTION OF THE INVENTION

Examples of the organic solvent which is insoluble in water include an aliphatic hydrocarbon, an aromatic hydrocarbon, a halogenated aliphatic hydrocarbon and a halogenated aromatic hydrocarbon. Examples of the aliphatic hydrocarbon include hexane, cyclohexene, heptane and octane. Examples of the aromatic hydrocarbon include benzene, toluene, ethylbenzene, p-xylene, o-xylene, m-xylene, mixed xylene, p-cymane, o-cymene and m-cymene. As the organic solvent which is insoluble in water, a hydrocarbon mixture such as ligroin and petroleum benzine can also be used. Examples of the halogenated aliphatic hydrocarbon include dichloromethane, chloroform, carbontetrachloride and 1,2-dichloroethane. Examples of the halogenated aromatic hydrocarbon include chlorobenzene and o-dichlorobenzene. These organic solvents can be used singly or as a mixture of two or more. Among the organic solvent mentioned above, aromatic hydrocarbons such as toluene, xylene and cymene, and halogenated aromatic hydrocarbons such as chlorobenzene and o-dichlorobenzene are preferred. Aromatic hydrocarbons such as toluene and xylene are particularly preferred.

Amount of the organic solvent used in the reaction is preferably from 0.9 to 3 parts by weight, more preferably from 1 to 3 parts by weight, particularly preferably from 1.5 to 2.5 parts by weight, per 1 part by weight of polyhydric phenol charged into the reaction. If amount of the organic solvent is too small, a large lump of crystal, which makes stirring difficult, tends to be produced. On the other hand, if amount of the organic solvent is too large, the reaction rate tends to be lowered.

In the present invention, water or seed crystal must exist in reaction mixture from the outset of the reaction in addition to the acid catalyst. In case when water is used, although amount of the water is not limited, usually it is preferred that the amount of water, including water coming from catalyst solution when the catalyst is added as an aqueous solution, or water of crystallization when the catalyst is hydrate, is from 0.1 to 1 part by weight per 1 part by weight of pure content of the catalyst. Seed crystal used in the present invention is a crystal of the hydroxyflavan compound of formula(1) to be prepared. Purity of seed crystal is not limited but usually, seed crystal having purity of 80% by weight or more is preferred. Amount of seed crystal is not particularly limited, but usually it is preferred that the amount is from 0.0001 to 1 part by weight per 1 part by weight of polyhydric phenol. Both of water and seed crystal may exist together in the reaction system from the outset of the reaction.

Polyhydric phenol used as a raw material of the present invention is represented by the formula(2) and it has 2-5 hydroxy groups. Although all of W, X, Y and Z may be hydroxy, some of W, X, Y and Z, which are same or different each other, may also be hydrogen, halogen, alkyl, alkenyl, cycloalkyl, aralkyl, arylalkenyl or aryl, provided that at least one of W, X, Y and Z is hydroxy. As examples of the halogen, fluorine, chlorine, bromine and iodine can be mentioned. As examples of the alkyl, alkyl having 1-5 carbon atoms such as methyl, ethyl and propyl, can be mentioned. As examples of the alkenyl, alkenyl having 2-5 carbon atoms, such as ethenyl and propenyl, can be mentioned. As examples of the cycloalkyl, cycloalkyl having 3-7 carbon atoms, such as cyclopentyl and cyclohexyl, can be mentioned. As examples of the aralkyl, aralkyl in which the alkyl portion has 1-3 carbon atoms, such as benzyl, phenethyl, naphthylmethyl, α-methylbenzyl and α,α-dimethylbenzyl can be mentioned. As examples of the arylalkenyl, arylalkenyl in which the alkenyl portion has 2-3 carbon atoms, such as styryl and α-methylstyryl can be mentioned. As examples of the aryl, phenyl and naphthyl can be mentioned. The cycloalkyl, aralkyl, arylalkenyl and aryl as W, X, Y and Z may be substituted by, for example, hydroxy or alkyl having 1-4 carbon atoms.

Among the polyhydric phenols mentioned above, dihydric or trihydric phenols which are not further substituted or which are substituted once by alkyl, aralkyl or arylalkenyl are preferred. Examples of the dihydric phenol include resorcin, 2-methylresorcin, 4-methylresorcin, 4-hexylresorcin, 4-tert-butylresorcin, 4-tert-octylresorcin, 4-styrylresorcin, 4-cumylresorcin (=4-α, α-dimethylbenzylresorcin), 4-(3-hydroxyphenyl) resorcin, 5-methylresorcin, catechol and hydroquinone. Examples of the trihydric phenol include pyrogallol, phloroglucin and hydroxyhydroquinone. Among them, more preferred is unsubstituted resorcin or resorcin substituted by alkyl at 2- or 4-position.

Ketone, another raw material used in the present invention, is reacted with the polyhydric phenol of formula (2) to produce the hydroxyflavan compound of formula(1). Ketches in which at least one of the hydrocarbon groups linked to the carbonyl group is an aliphatic group having a hydrogen atom at α-position, having α, β-unsaturated bond or having a hydroxy group at β-position are usually used in the present invention. As examples of the ketches, an aliphatic-aliphatic ketone or an aliphatic-aromatic ketone represented by the formula(3):

wherein $R^1$, $R^2$ and $R^3$ are as defined above, an α, β-unsaturated ketone represented by the formula(4):

wherein $R^1$, $R^2$, $R^4$ and $R^5$ are as defined above, or an β-hydroxy ketone represented by the formula(5):

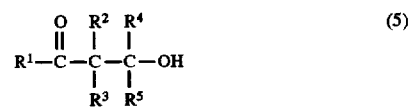

wherein $R^1$, $R^2$, $R^3$, $R^4$ and $R^5$ are as defined above, can be mentioned.

As alkyl denoted by $R^1$, $R^2$, $R^3$, $R^4$ or $R^5$ in the formulae (3), (4) or (5), alkyl having 1-5 carbon atoms is preferred and, when the alkyl has 3 or more carbon atoms, it may be either straight chain or branched chain alkyl. As examples of cycloalkyl denoted by $R^1$, $R^2$, $R^3$, $R^4$ or $R^5$, cycloalkyl having 3-7 carbon atoms such as cyclopentyl and cyclohexyl can be mentioned. As examples of aralkyl denoted by $R^1$, $R^2$, $R^3$, $R^4$ or $R^5$, aralkyl in which the alkyl portion has 1-3 carbon atoms and aralkyl in which the aryl portion is phenyl or naphthyl can be mentioned. As examples of aryl denoted by $R^1$, $R^2$, $R^3$, $R^4$ or $R^5$, phenyl and naphthyl can be mentioned. Ring portion of the cycloalkyl, aralkyl or aryl denoted by $R^1$, $R^2$, $R^3$, $R^4$ or $R^5$ may be substituted by lower alkyl such as alkyl having 1-4 carbon atoms.

$R^1$ and $R^2$ may form together with the carbon atoms to which they are attached a cycloalkane ring, such as a cycloalkane ring having 3-7 carbon atoms (i.e. the combination of $R^1$ and $R^2$ forms alkylene having 1-5 carbon atoms), particularly cyclopentane ring or cyclohexane ring. $R^4$ and $R^5$ may form together with the carbon atom to which they are attached a cycloalkane ring, such as a cycloalkane ring having 3-7 carbon atoms (i.e. the combination of $R^4$ and $R^5$ forms alkylene having 2-6 carbon atoms), particularly cyclopentane ring or cyclohexane ring. For example, a ketone of formula(3) may be a cyclic ketone in which $R^1$ and $R^2$ form together with the carbon atoms to which they are attached a cycloalkane ring, such as cyclopentane ring or cyclohexane ring. Among the ketones explained above, preferred examples include ketones of the formula (3), (4) or (5) wherein $R^1$, $R^4$ and $R^5$ are independently alkyl and $R^2$ and $R^3$ are independently hydrogen or alkyl, and ketches of the formula (3) wherein $R^3$ is hydrogen and $R^1$ and $R^2$ form together with the carbon atoms to which they are attached a cycloalkane ring.

Examples of the ketches of formula (3) include symmetric or asymmetric dialkylketones such as acetone, methylethylketone, diethylketone, ethylpropylketone and methylisobutylketone; cyclic ketches such as cyclopentanone and cyclohexanone; symmetric or asymmetric diaralkylketones; aralkylalkylketones such as benzylacetone; and arylalkylketones such as acetophenone.

As the ketones of formula (4), ketches wherein $R^1$, $R^4$ and $R^5$ are independently alkyl and $R^2$ is hydrogen or alkyl are preferred because of their easy obtainability, etc. Among them, more preferred examples from the view of obtainability are ketones represented by the formula (4a):

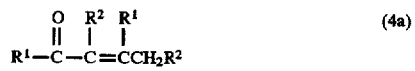

(4a)

wherein $R^1$ and $R^2$ are as defined above, because they are easy to obtain by dehydration dimerization of a ketone of formula(3) in which $R^1$ is alkyl, $R^2$ is hydrogen or alkyl and $R^3$ is hydrogen.

Examples of the ketches of formula (4) or (4a) include mesityl oxide, 5-methyl-4-hepten-3-one, 6-methyl-5-nonan-4-one and 5-ethyl-4-methyl-4-hepten-3-one.

As the ketones of formula (5), ketones wherein $R^1$, $R^4$ and $R^5$ are independently alkyl and $R^2$ is hydrogen or alkyl are preferred, considering their easy obtainability, etc. Among them, more preferred examples from the view of obtainability are ketones represented by the formula (5a):

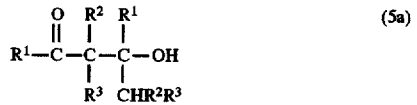

(5a)

wherein $R^1$, $R^2$ and $R^3$ are as defined above, because they are easy to obtain by dehydration dimerization of a ketone of formula(3) in which $R^1$ is alkyl and $R^2$ and $R^3$ are independently hydrogen or alkyl.

Examples of the ketones of formula (5) or (5a) include diacetone alcohol, 5-hydroxy-5-methylhepten-3-one, 6-hydroxy-6-methylnonan-4-one and 5-ethyl-5-hydroxy-4-methylhepten-3-one.

Among the ketones explained above, more preferred example include acetone, methylethylketone, diethylketone, ethylpropylketone, methylisobutylketone, benzylacetone, mesityloxide, acetophenone, cyclopentanone and cyclohexanone. As further preferred examples, acetone, diethylketone, methylethylketone and cyclohexanone can be mentioned.

Hydroxyflavan compounds of formula(1) may be produced by a condensation reaction of above-mentioned polyhydric phenols with above-mentioned ketones.

When ketones of formula(3) are used for the condensation reaction, hydroxyflavan compounds represented by the formula(1a):

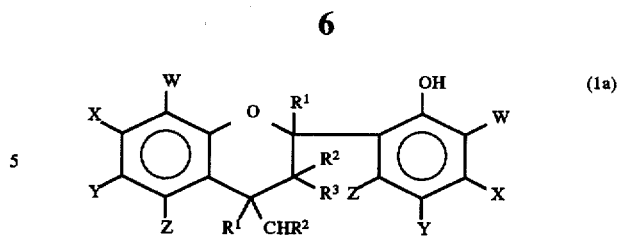

(1a)

wherein $R^1$, $R^2$, $R^3$, W, X, Y and Z are as defined above, are produced.

When ketones of formula(4) are used for the condensation reaction, hydroxyflavan compounds represented by the formula(1b):

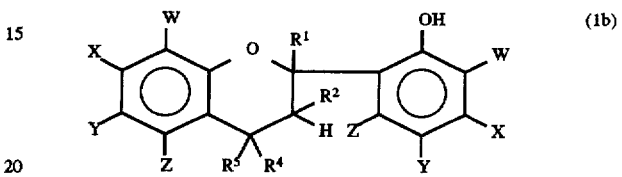

(1b)

wherein $R^1$, $R^2$, $R^4$, $R^5$, W, X, Y and Z are as defined above, are produced.

When ketones of formula(4a) are used for the condensation reaction, hydroxyflavan compounds represented by the formula(1c):

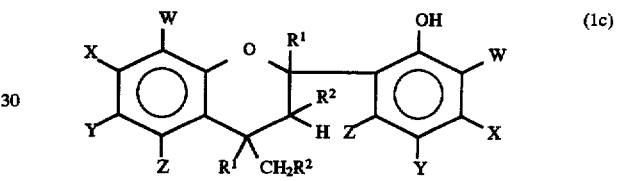

(1c)

wherein $R^1$, $R^2$, W, X, Y and Z are as defined above, are produced.

When ketones of formula(5a) are used for the condensation reaction, hydroxyflavan compounds of formula(1a) are produced.

In the formula(1,), $R^1$ and $R^2$ may form together with the carbon atoms to which they are attached a cycloalkane ring, such as a cycloalkane ring having 3-7 carbon atoms (i.e. the combination of $R^1$ and $R^2$ forms alkylene having 1-5 carbon atoms), particularly cyclopentane ring or cyclohexane ring. In the formula(1), $R^4$ and $R^5$ may form together with the carbon atom to which they are attached a cycloalkane ring, such as a cycloalkane ring having 3-7 carbon atoms (i.e. the combination of $R^4$ and $R^5$ forms alkylene having 2-6 carbon atoms), particularly cyclopentane ring or cyclohexane ring.

Among the hydroxyflavan compounds of formula(1) produced by the present invention, hydroxyflavan compounds of formula(1a) are preferred, considering raw material situation (which mean how easy the raw materials can be obtained). Among them, compounds of formula(1a) wherein $R^1$ is alkyl and $R^2$ and $R^3$ are independently hydrogen or alkyl, and compounds of formula(1a) wherein $R^3$ is hydrogen and $R^1$ and $R^2$ form together with the carbon atoms to which they are attached a cycloalkane ring are more preferably produced. Particularly, compounds of the formula(1a) wherein $R^1$ is alkyl and $R^2$ and $R^3$ are independently hydrogen or alkyl are preferably produced from the view of raw material situation.

In the formula(1), at least one of W, X, Y and Z must be hydroxy. Compounds of formula(1) wherein X is hydroxy are preferably produced, and the compounds of formula(1) wherein X is hydroxy and W, Y and Z are independently hydrogen and alkyl are more preferably produced.

As preferred examples of the hydroxyflavan compounds of formula(1) produced according to the present invention, following can be mentioned:

2,4,4-trimethyl-2',4',7-trihydroxyflavan,
2,4,4-trimethyl-2',3',4',7,8-pentahydroxyflavan,
2,3',4,4,8-pentamethyl-2',4',7-trihydroxyflavan,
2,4-diethyl-4-methyl-2',4',7-trihydroxyflavan,
4-ethyl-2,3,4-trimethyl-2',4',7-trihydroxyflavan,
2,4-diisobutyl-4-methyl-2',4',7-trihydroxyflavan,
4-isobutyl-2,4-dimethyl-3-isopropyl-2',4',7-trihydroxyflavan,
6-hydroxy-4a-(2,4-dihydroxyphenyl)-1,2,3,4,4a,9a-hexahydroxanthane-9-spiro-1'-cyclohexane [i.e. a compound of the formula(I) in which $W=Y=Z=R^3=H$, $X=OH$, $R^1$ and $R^2$ form tetramethylene in combination and $R^4$ and $R^5$ form pentamethylene in combination],
6-hydroxy-3a-(2,4-dihydroxyphenyl)-1,2,3,3a,9,9a-hexahydrocyclopenta[b]chromene-9-spiro-1'-cyclopentane [i.e. a compound of the formula(I) in which $W=Y=Z=R^3=H$, $X=OH$, $R^1$ and $R^2$ form trimethylene in combination and $R^4$ and $R^5$ form tetramethylene in combination],
and the like.

Although amounts of the raw materials are not limited, usually it is preferred that amount of the ketone is 0.5–2 equivalents based on 1 equivalent or the polyhydric phenol, i.e. when a ketone of formula(3) is used, amount of the ketone is 0.5–2 moles based on 1 mole of the polyhydric phenol, and when a ketone of formula(4) or (5) is used, amount of the ketone is 0.25–1 mole based on 1 mole of the polyhydric phenol.

From a economical view point, it is more preferred that amount of the ketone is 1–2 equivalents based on 1 equivalent of the polyhydric phenol, because, if amount of the ketone is small, particularly smaller than 1 equivalent based on 1 equivalent of the polyhydric phenol, reaction ratio of the polyhydric phenol lowers and refining process of the final product is required in order to remove unreacted polyhydric phenol. On the other hand, if amount of the ketone is too large, particularly when it exceeds 2 equivalents based on 1 equivalent of the polyhydric phenol, selectivity lowers.

Any acidic materials, for example a Brensted acid (protonic acid) or a Lewis acid, can be used in the present invention as the acid catalyst. Examples of the acid catalysts include inorganic acids or metal salts thereof such as phosphoric acid, polyphosphoric acid, sulfuric acid, hydrochloric acid and borofluoric acid; Lewis acids such as aluminum halogenate, zinc halogenate, tin halogenate, boron trifluoride, tin(II) triflate, ytterbium(III) triflate, lanthanum (III) triflate, cerium(III) triflate, neodymium(III) triflate, samarium(III) triflate, europium(III) triflate, gadolinium(III) triflate, lutetium(III) triflate and scandium(III) triflate; and organic acids such as oxalic acid, monochloroacetic acid, dichloroacetic acid, trichloroacetic acid, trifluoroacetic acid, maleic acid, fumaric acid, m-nitrobenzoic acid, p-toluenesulfonic acid, benzene sulfonic acid and trifluoromethan sulfonic acid. When the acid catalyst is a Brensted acid, its pKa value is preferably less than 3. If the reaction of the present invention is carried out in the presence of water from the outset, phosphoric acid is preferably used as the acid catalyst. The acid catalyst can be added into the reaction system as it is or as an aqueous solution of appropriate concentration.

Amount of the acid catalyst is not limited, but usually, 0.005–2 moles based on 1 mole of the polyhydric phenol is preferred. More preferred range varies depending on acid strength of the acid catalyst, etc. For example, when weak acids, i.e. acids having large pKa values such as phosphoric acid, oxalic acid, monochloro acetic acid, dichloro acetic acid, trichloro acetic acid, trifluoro acetic acid, maleic acid, fumaric acid and m-nitrobenzoic acid, or salts such as sodium hydrogensulfate, are used as the acid catalyst, 0.3–2 moles based on 1 mole of polyhydric phenol is the more preferred range. On the other hand, when strong acids such as sulfuric acid, hydrochloric acid, borofluoric acid, p-toluenesulfonic acid, benzene sulfonic acid and trifluoromethane sulfonic acid are used as the acid catalyst, 0.005–0.3 moles based on 1 mole of polyhydric phenol is the more preferred range.

Any order of charging polyhydric phenol, ketone, organic solvent, acid catalyst and water or seed crystal to the reaction mixture can be employed. As examples of the order;

charging polyhydric phenol, ketone, organic solvent, acid catalyst and water or seed crystal simultaneously;

adding ketone continuously or intermittently into a mixture of polyhydric phenol, organic solvent, acid catalyst and water or seed crystal;

adding acid catalyst continuously or intermittently into a mixture of polyhydric phenol, ketone, organic solvent, and water or seed crystal;

and the like can be mentioned. When ketone or acid catalyst is added dropwise, the adding rate is not limited. However, usually, 0.1–1 mole/hour per 1 mole of polyhydric phenol is preferred in case of ketone added dropwise, and 0.05–0.1 mole/hour per 1 mole of polyhydric phenol is preferred in case of acid catalyst added dropwise. If desired, inner part of a reaction vessel may be replaced with an inert gas such as nitrogen gas before charging raw material or during the reaction being conducted.

Although reaction temperature is not limited, usually it is from 30° C. to reflux temperature. Although reaction time is not limited, usually it is from 1 to 20 hours. Preferably, reaction should be continued until reaction ratio of polyhydric phenol exceeds 80%.

Hydroxyflavan compound of the formula(1) produced in the reaction deposits as crystal during the reaction. Methods for separating the deposited hydroxyflavan compound of the formula(1) from reaction system and methods for refining the compound are not limited. Usually, it is preferred that, after completion of the reaction, the deposited hydroxyflavan compound is subjected to a solid-liquid separation such as filtration and washed with water to remove catalyst and unreacted raw materials contained in wet cake. Recrystallization and the like may also be carried out to obtain high purity hydroxyflavan compound.

PRERRED EMBODIMENTS

The present invention will be explained more particularly with the following Examples which shall not be construed as limiting the scope of the invention in any way. In the Examples, "%" means "% by weight" unless otherwise mentioned.

EXAMPLE 1

Into a four necked flask equipped with a thermometer, a condenser, a dropping funnel and a stirrer, 55.1 g (0.5 mole) of resorcin, 100 g of toluene and 28.8 g (0.25 mole) of 85% aqueous phosphoric acid solution were charged at a room temperature. After the inner part of the flask was replaced with nitrogen gas, the inner temperature was elevated to 60° C. Then, 31.9 g (0.55 mole) of acetone was added dropwise thereto. After completion of the dropwise addition, the mixture was reacted for 8 hours under refluxing conditions.

After completion of the reaction, deposited crystal produced during the reaction was filtered at a room temperature, washed with water and dried to obtain 74.1 g of colorless powder.

By measuring $^1$H NMR spectrum and Mass spectrum, the colorless powder was identified as 2,4,4-trimethyl-2',4',7-trihydroxyflavan.

$^1$H NMR spectrum (measured by using GX-270 manufactured by Nippon Denshi Co., Ltd.) Chemical Shift ppm (solvent: acetone-d6, TMS) 0.67 (s, 3H); 1.19 (s, 3H); 1.65 (s, 3H); 1.85 (d, J=14 Hz, 1H); 2.95 (d, J=14 Hz, 1H); 6.15 (d, J=7 Hz, 1H); 6.3–6.5 (multi, 3H); 6.95 (d, J=7 Hz, 1H); 8.05 (s, 1H); 8.09 (s, 1H); 8.45 (s, 1H)

Mass spectrum (FD/MS) m/e: 300

The result i.e. conversion of resorcin, selectivity and purity of 2,4,4-trimethyl-2',4',7-trihydroxyflavan after dried and yield of 2,4,4-trimethyl-2',4',7-trihydroxyflavan based on charged resorcin are shown in Table 1.

EXAMPLE 2

Example 1 was repeated except that amount of acetone was changed to 58.1 g (1.0 mole) and reaction time was also changed to 12 hours to obtain 65.4 g of 2,4,4-trimethyl-2',4',7-trihydroxyflavan.

The results are shown in Table 1.

EXAMPLE 3

Example 1 was repeated except that amount of 85% aqueous phosphoric acid solution was changed to 14.4 g (0.13 mole) and reaction time was also changed to 4 hours to obtain 58.8 g of 2,4,4-trimethyl-2',4',7-trihydroxyflavan.

The results are shown in Table 1.

EXAMPLE 4

Example 1 was repeated except that toluene was replaced with chlorobenzene to obtain 74.2 g of 2,4,4,-trimethyl-2',4',7-trihydroxyflavan.

The results are shown in Table 1.

EXAMPLE 5

Example 1 was repeated except that toluene was replaced with ethylbenzene and reaction time was also changed to 4 hours to obtain 64.9 g of 2,4,4-trimethyl-2',4',7-trihydroxyflavan.

The results are shown in Table 1.

EXAMPLE 6

Example 1 was repeated except that toluene was replaced with p-cymene and reaction time was also changed to 4 hours to obtain 78.4 g of 2,4,4-trimethyl-2',4',7-trihydroxyflavan.

The results are shown in Table 1.

EXAMPLE 7

Into a four necked flask equipped with a thermometer, a condenser, a dropping funnel and a stirrer, 55.1 g (0.5 mole) of resorcin, 31.9 g (0.55 mole) of acetone and 100 g of toluene were charged at a room temperature, After the inner part of the flask was replaced with nitrogen gas and the inner temperature was elevated to 40° C., 34.5 g (0.25 mole) of hydrated sodium hydrogensulfate and 5 g of water were charged. Thereafter, the inner part of the flask was replaced with nitrogen again and the mixture was reacted for 4 hours under refluxing conditions. After completion of the reaction, deposited crystal of the reaction product was filtered at a room temperature, washed with water and dried to obtain 75.2 g of powder of 2,4,4-trimethyl-2',4',7-trihydroxyflavan.

The results are shown in Table 1.

EXAMPLE 8

Into a four necked flask equipped with a thermometer, a condenser, a dropping funnel and a stirrer, 55.1 g (0.5 mole) of resorcin, 31.9 g (0.55 mole) of acetone and 100 g of toluene were charged at a room temperature. After the inner part of the flask was replaced with nitrogen gas and the inner temperature was elevated to 40° C., 2.5 g (0.008 mole) of 2,4,4-trimethyl-2',4',7-trihydroxyflavan as seed crystal and 0.95 g (0.005 mole) of hydrated p-toluenesulfonic acid as acid catalyst were added. Thereafter, the inner part of the flask was replaced with nitrogen again and the mixture was reacted for 14 hours under refluxing conditions. After completion of the reaction, deposited crystal of the reaction product was filtered at a room temperature, washed with water and dried to obtain 70.9 g of powder of 2,4,4-trimethyl-2',4',7-trihydroxyflavan.

The results are shown in Table 1.

EXAMPLE 9 (FOR COMPARISON)

Into a four necked flask equipped with a thermometer, a condenser, a dropping funnel and a stirrer, 110.1 g (1.0 mole) of resorcin, 24.3 g (0.24 mole) of 36% hydrochloric acid and 100 g of water were charged. After the inner temperature was elevated to 35° C., 29.0 g (0.5 mole) of acetone was added dropwise. After completion of the dropwise addition, the mixture was reacted for 3 hours at 35° C., then, cooled to a room temperature, and, thereafter, further stirred for 14 hours. Then, deposited crystal of the reaction product was filtered at a room temperature, washed with water and dried to obtain 64.2 g of powder of 2,4,4-trimethyl-2',4',7-trihydroxyflavan.

The results are shown in Table 1.

EXAMPLE 10 (FOR COMPARISON)

Into a four necked flask equipped with a thermometer, a condenser, a dropping funnel and a stirrer, 55.1 g (0.5 mole) of resorcin and 31.9 g (0.55 mole) of acetone were charged. After the inner temperature was elevated to 60° C., 28.8 g (0.25 mole) of 85% aqueous phosphoric acid solution was added dropwise. After completion of the dropwise addition, the mixture was reacted for 1 hours at 80° C. and resinous material was obtained.

The results are shown in Table 1.

TABLE 1

| Example No. | Conversion of Resorcin (%) | Selectivity #1) (%) | Purity #2) (%) | Yield #3) (%) |
|---|---|---|---|---|
| 1 | 99.5 | 91.4 | 91 | 90 |
| 2 | 98.4 | 84.2 | 96 | 83 |
| 3 | 85.6 | 86.0 | 93 | 73 |
| 4 | 99.3 | 80.2 | 81 | 80 |
| 5 | 97.8 | 78.6 | 89 | 77 |
| 6 | 97.6 | 71.1 | 66 | 69 |

TABLE 1-continued

| Example No. | Conversion of Resorcin (%) | Selectivity #1) (%) | Purity #2) (%) | Yield #3) (%) |
|---|---|---|---|---|
| 7 | 85.6 | 93.6 | 80 | 80 |
| 8 | 93.1 | 80.1 | 79 | 75 |
| 9 | 36.4 | 98.4 | 85 | 36 |
| 10 | 82.9 | 54.7 | 45 | 45 |

1) Calculated according to the following equation: Selectivity = [2 × (Mole amount of Hydroxyflavan compound produced) × 100]/[(Reaction ratio of resorcin (%)/100) × Mole amount of the charged resorcin].
2) Measured by using HPLC (absolute calibration method; compared to standard samples). Round to the nearest whole number.
3) Based on the amount of charged resorcin. Round to the nearest whole number.

EXAMPLE 11

By conducting same procedures as Example 1 except that acetone is replaced with 0.5 mole of mesityl oxide, 2,4,4-trimethyl-2',4',7-trihydroxyflavan can be obtained.

EXAMPLE 12

By conducting same procedures as Example 1 except that acetone is replaced with 0.5 mole of diacetonealcohol, 2,4,4-trimethyl-2',4',7-trihydroxyflavan can be obtained.

According to the present invention, hydroxyflavan compounds of formula(1) can be obtained in high yield and high selectivity while maintaining high conversion of the polyhydric phenol.

What we claim:

1. A process for preparing a hydroxyflavan compound represented by formula(1):

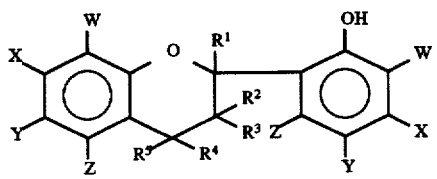

wherein $R^1$, $R^4$ and $R^5$ each independently represent alkyl, cycloalkyl, aralkyl or aryl, and $R^2$ and $R^3$ each independently represent hydrogen, alkyl, cycloalkyl, aralkyl or aryl, or $R^1$ and $R^2$ form together with the carbon atoms to which they are attached a cycloalkane ring, or $R^4$ and $R^5$ form together with the carbon atom to which they are attached a cycloalkane ring; and W, X, Y and Z each independently represent hydrogen, halogen, hydroxy, alkyl, alkenyl, cycloalkyl, aralkyl, arylalkenyl or aryl, provided that at least one of W, X, Y and Z is hydroxy;

which process comprises reacting a polyhydric phenol compound represented by formula(2):

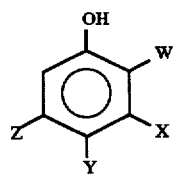

wherein W, X, Y and Z are as defined above with a ketone in the presence of (i)an acid catalyst and (ii)water and/or a seed crystal, using an organic solvent which is insoluble in water.

2. A process according to claim 1 wherein the ketone is represented by the formula(3):

wherein $R^1$, $R^2$ and $R^3$ are as defined in claim 1.

3. A process according to claim 1 wherein the ketone is represented by the formula(4) or (5):

or

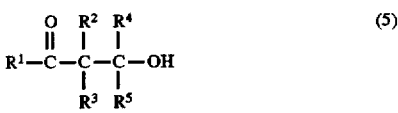

wherein $R^1$, $R^2$, $R^3$, $R^4$ and $R^5$ are as defined in claim 1.

4. A process according to claim 3 wherein the ketone is represented by the formula(4a) or (5a):

or

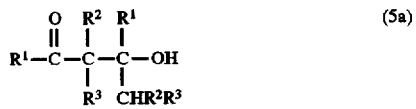

wherein $R^1$, $R^2$ and $R^3$ are as defined in claim 1.

5. A process according to claim 2 wherein X is hydroxy, $R^1$ is alkyl and $R^2$ and $R^3$ are independently hydrogen or alkyl.

6. A process according to claim 1 wherein the hydroxyflavan compound of the formula(1) is 2,4,4-trimethyl-2',4',7-trihydroxyflavan; the polyhydric phenol compound of the formula(2) is resorcin; and the ketone is acetone.

7. A process according to claim 1 wherein the organic solvent which is insoluble in water is an aliphatic hydrocarbon, an aromatic hydrocarbon, a halogenated aliphatic hydrocarbon or a halogenated aromatic hydrocarbon.

8. A process according to claim 1 wherein the organic solvent which is insoluble in water is an aromatic hydrocarbon or a halogenated aromatic hydrocarbon.

9. A process according to claim 1 wherein the amount of ketone is 0.5–2 equivalents per 1 equivalent of polyhydric phenol.

10. A process according to claim 1 wherein the acid catalyst is a protonic acid having a pKa value of less than 3.

11. A process according to claim 1 wherein the amount of the acid catalyst is 0.005–2 moles per 1 mole of polyhydric phenol.

12. A process according to claim 1 wherein the amount of organic solvent is 0.9–3 parts by weight per 1 part by weight of polyhydric phenol.

13. A process according to claim 1 wherein the amount of water is 0.1–1 part by weight per 1 part by weight of acid catalyst, calculated as the weight of the pure anhydrous acid, at the outset of the reaction.

14. A process according to claim 13 wherein the acid catalyst is phosphoric acid.

15. A process according to claim 1 wherein the amount of seed crystal is 0.0001–1 part by weight per 1 part by weight of polyhydric phenol at the outset of the reaction.

16. A process according to claim 4 wherein X is hydroxy, $R^1$ is alkyl and $R^2$ and $R^3$ are independently hydrogen or alkyl.

* * * * *